United States Patent
Barzell et al.

(10) Patent No.: US 7,172,579 B2
(45) Date of Patent: Feb. 6, 2007

(54) SYSTEM AND METHOD FOR IRRIGATION AND TISSUE EVACUATION AND COLLECTION

(75) Inventors: Winston E. Barzell, Sarasota, FL (US); Willet F. Whitmore, Sarasota, FL (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 53 days.

(21) Appl. No.: 10/841,074

(22) Filed: May 7, 2004

(65) Prior Publication Data

US 2005/0054995 A1    Mar. 10, 2005

Related U.S. Application Data

(60) Provisional application No. 60/501,263, filed on Sep. 9, 2003, provisional application No. 60/553,067, filed on Mar. 15, 2004.

(51) Int. Cl.
*A61M 5/178* (2006.01)
*A61M 1/00* (2006.01)

(52) U.S. Cl. .................. 604/185; 604/187; 604/319
(58) Field of Classification Search .................. 604/27, 604/37, 514, 517, 183, 185, 317, 319, 187
See application file for complete search history.

(56) References Cited

U.S. PATENT DOCUMENTS

| | | | |
|---|---|---|---|
| 764,996 A | 7/1904 | Ellis | |
| 873,728 A * | 12/1907 | Crisenberry | 604/37 |
| 877,926 A | 2/1908 | Hilker | |
| 1,015,895 A | 1/1912 | Kelley | |
| 1,484,621 A | 2/1924 | Bond et al. | |
| 1,493,592 A | 5/1924 | Beck | |
| 1,925,230 A * | 9/1933 | Buckhout | 604/215 |
| 3,233,609 A | 2/1966 | Leucci | 128/227 |
| 3,429,313 A | 2/1969 | Romanelli | 128/276 |

(Continued)

FOREIGN PATENT DOCUMENTS

FR    2 592 584    7/1987

(Continued)

OTHER PUBLICATIONS

R. Misra and H. Grundsell, "The Ellik evacuator. A reinvention." *Surgical Endoscopy*, vol. 15, No. 3, 2001, p. 329.

(Continued)

*Primary Examiner*—Sharon Kennedy
(74) *Attorney, Agent, or Firm*—Steptoe & Johnson LLP

(57) ABSTRACT

The present invention provides a system and method for irrigating and collecting tissue from a body cavity in a patient. The system includes an irrigation and collection device for injecting an irrigation fluid into the body cavity. The irrigation device injects fluid into the body cavity by creating a positive pressure within the device to expel the irrigation fluid from the device into the body cavity. The irrigation fluid is evacuated from the body cavity by the resulting negative pressure within the device, drawing the irrigation fluid and any loose tissue or particulate material into the device. The irrigation fluid is filtered, collecting the evacuated tissue and particulate material in a collection receptacle thereby isolating the evacuated tissue and particulate material within the irrigation fluid.

58 Claims, 7 Drawing Sheets

U.S. PATENT DOCUMENTS

| | | | |
|---|---|---|---|
| 3,471,064 A | 10/1969 | Micallef | 222/211 |
| 3,636,940 A | 1/1972 | Gravlee | 128/2 B |
| 3,785,380 A | 1/1974 | Brumfield | 128/276 |
| 3,818,907 A | 6/1974 | Walton | 128/172.2 |
| 3,831,605 A | 8/1974 | Fournier | 128/263 |
| 3,892,226 A * | 7/1975 | Rosen | 600/563 |
| 3,908,660 A | 9/1975 | Kaplan et al. | 128/305 |
| D246,187 S | 10/1977 | DeArment | D24/14 |
| 4,221,225 A * | 9/1980 | Sloan | 600/563 |
| 4,282,873 A | 8/1981 | Roth | 128/276 |
| 4,519,385 A | 5/1985 | Atkinson et al. | 128/66 |
| 4,594,073 A | 6/1986 | Stine | 604/187 |
| 4,676,777 A | 6/1987 | Watts | 604/33 |
| 4,729,764 A | 3/1988 | Gualtier | 604/38 |
| 4,776,840 A | 10/1988 | Freitas et al. | 604/33 |
| 4,787,889 A | 11/1988 | Steppe et al. | 604/22 |
| 4,801,292 A | 1/1989 | Watson | 604/36 |
| 4,806,101 A | 2/1989 | Rossi | 433/92 |
| 4,842,581 A | 6/1989 | Davis | 604/38 |
| 4,872,866 A | 10/1989 | Davis | 604/227 |
| 4,880,408 A * | 11/1989 | Cumes et al. | 604/36 |
| 4,968,303 A | 11/1990 | Clarke et al. | 604/187 |
| 4,976,682 A | 12/1990 | Lane et al. | 604/4 |
| 5,049,135 A | 9/1991 | Davis | 604/181 |
| 5,049,141 A | 9/1991 | Olive | 604/891.1 |
| 5,078,690 A | 1/1992 | Ryan | 604/187 |
| 5,115,816 A | 5/1992 | Lee | 128/749 |
| 5,241,969 A | 9/1993 | Carson et al. | 128/753 |
| 5,250,065 A | 10/1993 | Clement et al. | 606/172 |
| 5,254,086 A | 10/1993 | Palmer et al. | 604/38 |
| 5,306,237 A | 4/1994 | Clement et al. | 604/30 |
| 5,314,406 A | 5/1994 | Arias et al. | 604/21 |
| 5,330,424 A | 7/1994 | Palmer et al. | 604/28 |
| 5,338,292 A | 8/1994 | Clement et al. | 604/22 |
| 5,338,294 A * | 8/1994 | Blake, III | 604/38 |
| 5,374,244 A | 12/1994 | Clement et al. | 604/32 |
| 5,421,824 A * | 6/1995 | Clement et al. | 604/29 |
| 5,469,860 A | 11/1995 | De Santis | 128/765 |
| 5,492,535 A | 2/1996 | Reed et al. | 604/152 |
| 5,505,210 A | 4/1996 | Clement | 128/753 |
| 5,529,463 A | 6/1996 | Layer et al. | 417/403 |
| 5,647,852 A | 7/1997 | Atkinson | 604/151 |
| 5,667,500 A | 9/1997 | Palmer et al. | 604/283 |
| 5,746,721 A | 5/1998 | Pasch et al. | 604/153 |
| 5,779,702 A | 7/1998 | Fard | 606/53 |
| 5,830,152 A | 11/1998 | Tao | 600/562 |
| 5,843,022 A | 12/1998 | Willard et al. | 604/30 |
| 5,941,851 A | 8/1999 | Coffey et al. | 604/131 |
| 6,090,094 A | 7/2000 | Clifford, Jr. et al. | 604/500 |
| 6,264,636 B1 * | 7/2001 | Holm et al. | 604/183 |

FOREIGN PATENT DOCUMENTS

GB     2 136 690 A     9/1984

OTHER PUBLICATIONS

A. A. Fiore et al., "Evacuatore vescicale Urovac: confronto con i dispositivi tradizionalmente usati" (translation "Bladder evacuation device 'Urovac': comparison with the conventional most used devices"), *Minerva Urologica e Nefrologica*, vol. 47, No. 2, Jun. 1995, pp. 97-98.

John A. Hutch, "Modification of the Ellik evacuator," *The Journal of Urology*, vol. 68, No. 3, Sep. 1952, pp. 661-662.

* cited by examiner

SYSTEM AND METHOD FOR IRRIGATION AND TISSUE EVACUATION AND COLLECTION

CROSS-REFERENCE TO RELATED APPLICATIONS

This application claims the benefit under 35 U.S.C § 119 (e) of U.S. Provisional Patent Application No. 60/501,263, filed Sep. 9, 2003 and entitled SYSTEM FOR IRRIGATION AND TISSUE EVACUATION AND COLLECTION, and U.S. Provisional Patent Application No. 60/553,067, filed Mar. 15, 2004 and also entitled SYSTEM FOR IRRIGATION AND TISSUE EVACUATION AND COLLECTION, the entirety of which are incorporated herein by reference.

FIELD OF THE INVENTION

The present invention relates to an irrigation and tissue evacuation and collection system and method for use in medical procedures.

BACKGROUND OF THE INVENTION

A number of medical procedures involve the irrigation of a body cavity. For example, it is necessary to irrigate the urinary bladder during many endoscopic urologic procedures to flush out (and in some cases collect) blood clots, pieces of tissue, and the like. The general approach to accomplish this is to introduce a sterile saline solution or water into the bladder and then withdraw the fluid which has mixed and suspended material to be removed. This process needs to be repeated until the withdrawn fluid becomes clear and satisfactorily free of particulate material.

Presently, the most common device used for bladder irrigation is the Ellik evacuator. The Ellik evacuator consists of a clear hourglass-shaped bowl with rubber bulb and nozzle fitted to the upper bowl for circulating solution through the urethra and the bladder. The bulb is opaque and oriented at a right angle to the axis of the hourglass. Because of this, one problem with the Ellik evacuator-is the difficulty in fluid filling and air purging. Tissue found in the return flow of solution ideally is collected in the lower chamber. Tissue collects there due to the effects of gravity. Thus, another limitation of the Ellik evacuator is that the entrained tissue must settle by gravity into the lower chamber. As a result, only the particulate and tissue of a specific gravity greater than that of the sterile solution will settle into the lower chamber. The particulate in suspension in the upper chamber tends to be reintroduced into the bladder when the bulb is again compressed. Also, tissue or particulate matter is often sucked into the bulb regardless of specific gravity and because of the opacity of the bulb, tissue caught there cannot be visualized and may become lost. In order to prevent the recirculation of contaminated solution created by the initial irrigation with the Ellik evacuator, the surgeon must empty and refill the Ellik repeatedly until the final irrigation remains clear. In addition to this repetitive exercise, each time the Ellik evacuator is emptied and refilled, the tissue that has accumulated in the irrigant must be filtered and removed from the basin by hand at the conclusion of the irrigation. During this step, tissue is occasionally lost on the table or floor and there are significant blood and tissue exposure risks to operating room personnel. A final problem with the Ellik is that the rubber bulb is plugged like a stopper into a smooth glass tubular port. Since the neck of the bulb is smooth and cylindrical, there is only friction without mechanical advantage to hold them together. Consequently, the bulb may easily detach from the glass container inadvertently during handling with the result that the glass container can crash to the floor and shatter.

A number of attempts have been made to improve upon the Ellik evacuator. These efforts include the devices described in U.S. Pat. Nos. 3,892,226; 4,282,873; 4,729,764, 4,801,292; 5,338,294; and 5,421,824. In addition to their own unique limitations, all of the devices taught by these patents fail to duplicate the ideal degree and velocity of fluid turbulence that is generated with the Ellik evacuator. Furthermore, none of these devices have a readily transferable tissue collecting mechanism. For example, in U.S. Pat. No. 5,421,824, a squeezable portion of the container forces fluid from the container into the body cavity and by releasing the compressional forces allows the squeezable portion to expand and withdraw the fluid. Unfortunately, the fluid turbulence generated by this squeezable portion, and specifically the negative pressure generated when releasing the compressional forces, is inadequate and does not match those of the Ellik evacuator. Moreover, there is often leakage of fluid at the juncture of the container and its cap. Additionally, while this patent prevents particulate tissue from reentering the body cavity, it does not have a readily transferable tissue collecting mechanism and thus suffers from the same limitation as the Ellik evacuator in that the tissue collected by the device must be filtered and removed from the basin by hand at the conclusion of the irrigation. During this step, tissue is occasionally lost on the table and floor and there is significant blood and tissue exposure risk to operating room personnel in this maneuver.

Thus, there remains a need for an improved irrigation and tissue evacuation and collection system.

SUMMARY OF THE INVENTION

The present invention relates to a medical irrigation and tissue collection system for introducing fluid into and withdrawing fluid from a body cavity via a fluid line. The system includes a container having an interior for holding fluid; a pump bulb in fluid communication with the container that may be securely attached using means other than pure friction; a tube having a first end portion connected with the fluid line and a second end portion in fluid communication with the interior of the container; and a collection receptacle for collecting particulate material. The collection receptacle is located within the interior of the container and removably connected to the second end portion of the fluid line. The collection receptacle is provided with a plurality of openings allowing the passage of fluid and particulate material smaller than a predetermined size.

In one embodiment, the second end portion has a perforated section with a plurality of pores allowing the passage of fluid and particulate material of a given size. The relative sizes of the pores and opening can be selected as desired. For example, the size of the opening, on average, can be larger than the size of the pores, on average. Thus, smaller and intermediate sized particles can more readily move freely in and out of collection receptacle than through the second end portion of the tube, allowing for the collection of the larger size particles in the collection receptacle.

A one-way valve can be operatively associated with the tube allowing fluid and particulate material to flow through the tube and pass into the collection receptacle. The one-way valve can be coupled to the second end portion of the tube and include a length of tubing collapsible under a pressure differential generated by the pump bulb.

The collection receptacle can be a basket made of a rigid polymeric material. Alternatively, the collection receptacle can be a mesh bag. As an alternative to the use of a one-way valve or as a supplement thereto, the mesh bag can be collapsible under a pressure differential generated by the pump bulb.

A cap can be removably coupled to the container with a pump conduit having a first end portion extending from the cap and a second end portion coupled to the pump bulb. The pump conduit can extend from the cap at a right angle or downwardly from the cap at a non-orthogonal angle. In an exemplary embodiment, the container has upper and lower portions with the cap removably coupled to the upper portion and the collection receptacle located within the lower portion of the container.

The upper and lower portions of the container can be configured and dimensioned such that turbulent flow resulting from the pressure generated by compressing the pump bulb is greater in the upper portion of the container compared to the lower portion of the container. Furthermore, the basket can be positioned to experience substantially no turbulent flow from the pressure generated by compressing the pump bulb. The cap can define a cap interior such that turbulent flow resulting from the pressure generated by compressing the pump bulb is substantially limited to the cap interior.

A flow restrictor can be located between the cap interior and the upper portion of the container. In one embodiment, the flow restrictor is a lipped portion of the cap. In a second embodiment the flow restrictor is an external flange attached to the interior tube.

The present invention also relates to a method of collecting tissue and particulate material from a body cavity in a patient. The method comprises positioning a medical irrigation and tissue collection device in fluid communication with the body cavity; injecting an irrigation fluid from the medical irrigation and tissue collection device into the body cavity and evacuating the irrigation fluid from the body cavity into the medical irrigation and tissue collection device. As the evacuated irrigation fluid includes tissue and particulate material from the body cavity, the evacuated irrigation fluid is filtered to isolate the tissue and particulate material within the irrigation fluid. The filtering is performed such that the tissue and particulate material of a minimum chosen size is collected in a collection receptacle within the medical irrigation and tissue collection device.

The injection of the irrigation fluid from the medical irrigation and tissue collection device into the body cavity can include creating a positive pressure within the irrigation and tissue collection device into the body cavity. This creates a turbulent flow in an upper portion of the medical irrigation and tissue collection device while maintaining a substantially turbulent free flow in a lower portion of the medical irrigation and tissue collection device. The filtering of the evacuated irrigation fluid to isolate the tissue and particulate material within the irrigation fluid can include collecting the tissue and particulate material in the lower portion of the medical irrigation and tissue collection device. The steps can be repeated as desired.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention provides a system and method for irrigating and collecting tissue from a body cavity in a patient. The system includes an irrigation and collection device for injecting an irrigation fluid into the body cavity. The irrigation device injects fluid into the body cavity by creating a positive pressure within the device to expel the irrigation fluid from the device into the body cavity. The irrigation fluid is evacuated from the body cavity by the resulting negative pressure within the device, drawing the irrigation fluid and any loose tissue or particulate material into the device. The irrigation fluid is filtered to collect the evacuated tissue and particulate material in a collection receptacle.

To repeat the process, the positive pressure is created within the device, expelling the irrigation fluid from the device into the body cavity. During the expulsion of the irrigation fluid, the previously collected tissue and particulate material are retained within the collection receptacle, such that they do not re-enter the body cavity with the expelled irrigation fluid. The irrigation fluid is again evacuated from the body cavity by the resulting negative pressure within the device, drawing the irrigation fluid and any loose tissue or particulate material into the device. The irrigation fluid is filtered to collect the additional evacuated tissue and particulate material in the collection receptacle. The process can be repeated as desired to remove substantially all of the loose tissue and particulate material from the body cavity.

Figure 1:
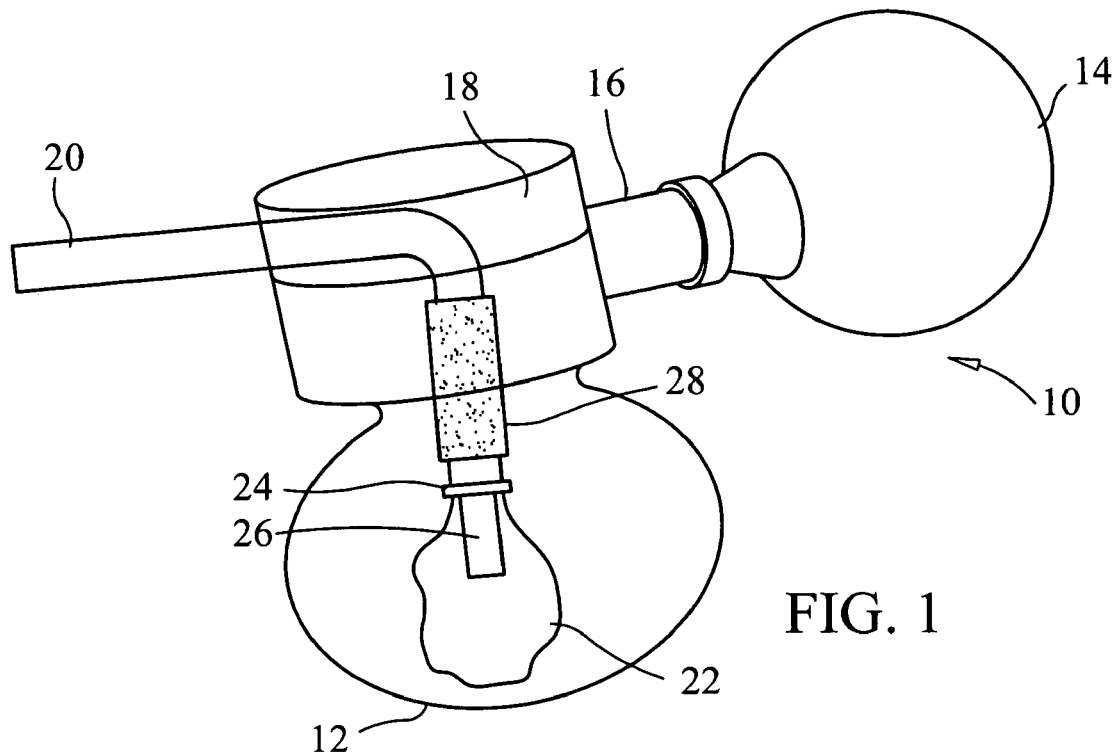
FIG. 1 is a perspective view of an embodiment of the system according to the present invention.
Figure 2:
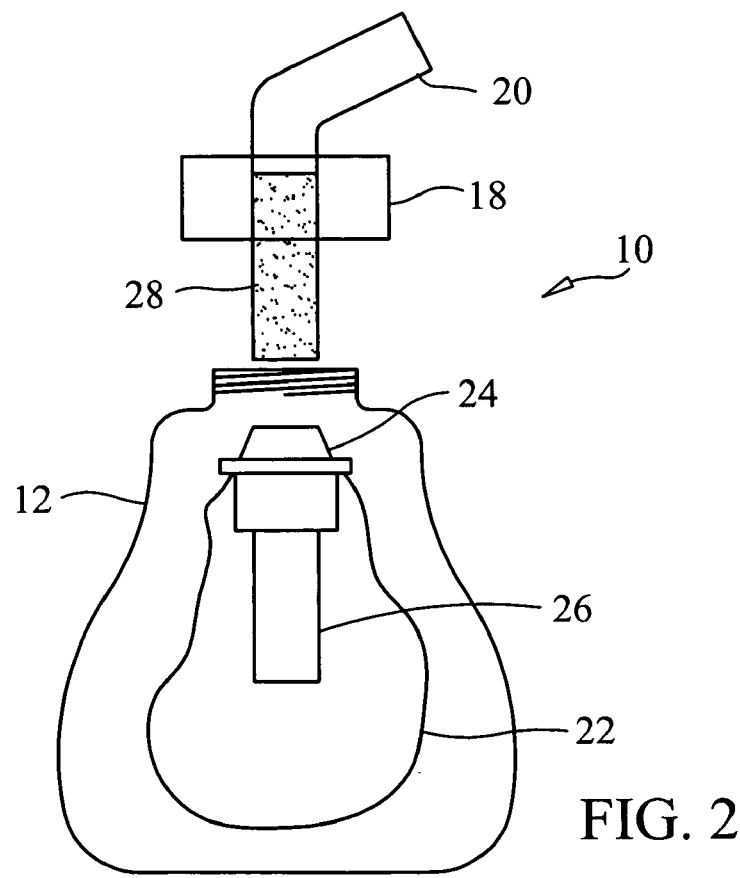
FIG. 2 is a side view of the system of FIG. 1 with the cap disconnected from the fluid vessel and the pump bulb removed.

Referring now to the drawing figures in which like reference numerals refer to like elements, there is shown in FIGS. 1 and 2 an irrigation and tissue evacuation and collection system 10 of the present invention. The irrigation and tissue evacuation and collection system 10 includes a container 12 for holding irrigation fluid. The irrigation fluid can be any fluid used for irrigation or lavage, such as a sterile normal saline solution or a sterile water solution. A pump bulb 14 is coupled to container 12 via a pump conduit 16. Although pump conduit 16 is shown as attached to container 12, pump conduit 16 could be connected to a removable cap 18. Cap 18 is shown as connected to container 12 by threads, but other coupling mechanisms could be used.

Pump bulb 14 is made of a resilient material such that as pump bulb 14 is squeezed, positive pressure is created to force irrigation fluid from container 12. When the squeezing force is removed, pump bulb 14 returns to its non-compressed state, thereby creating negative pressure to draw irrigation fluid into container 12. Although pump bulb 14 is shown frictionally connected to the pump conduit 16, other coupling mechanism could be used. For example, the pump conduit 16 can be internally (or externally) threaded, for threadably receiving the pump bulb 14, which would have corresponding threads. The mating threads may provide a more secure connection than a simple friction fit. This is beneficial since the pump bulb may be the only portion of the device held by the clinician. It should be noted that any suitable pump member could be used as an alternative to pump bulb 14.

A tube 20 provides the pathway for the irrigation fluid into and out of container 12. Tube 20 has a first end coupled to a fluid line (not shown) that is insertable into the patient body cavity that is being treated (for example through the working channel of an endoscope), e.g. a bladder to remove prostatic tissue chips after a transurethral resectioning (TUR) procedure. The second end of tube 20 is in fluid communication with the interior of container 12. In this embodiment, the second end is coupled to a collection bag 22 via a releasable connector 24 (e.g. an o-ring) so that collection bag 22 can be removed.

In use, collection bag 22 is located within the interior of container 12 and is used to obtain samples of particulate materials. Collection bag 22 is provided with a plurality of openings allowing the passage of fluid and particulate material of a given size. The openings in the collection bag 22 have a size to restrict throughflow of particulate material of a predetermined size. As collection bag 22 can be made of a mesh type material, such as a mesh fabric bag, different bags having a range of mesh size openings can be used to suit a particular application. For example, if large tissue particles are desired to be collected, a collection bag having relatively large mesh size openings would be used. Also, a series of collection bags 22 could be used so that samples containing particles of different sizes could be obtained.

In the manufacture of collection bag 22, the size and shape of the openings may not necessarily be uniform. This may result in a variety of shapes of the openings and a range of sizes of the openings (for example the cross sectional opening areas). Accordingly and as is customary in the art, the openings in collection bag 22 can be referred to as having an average size.

Tube 20 also includes a filter 28 such as a fenestrated portion that allows fluid, but not particulate material, to circulate in and out of container 12. Filter 28 is provided with a plurality of pores allowing the passage of fluid and particulate material of a given size. The pores in filter 28 have a size to restrict throughflow of particulate material of a predetermined size. Similar to collection bag 22, in the manufacture of filter 28, the size and shape of the pores may not necessarily be uniform. This may result in a variety of shapes of the pores and a range of sizes of the pores (for example the cross sectional pore area). Accordingly and as is customary in the art, the pores of filter 28 can be referred to as having an average size.

The relative sizes of the openings (in collection bag 22) and the pores (in filter 28) can be adjusted as desired to a particular clinical situation. For example, the pores on filter 28 can be made to have an average size that is smaller than the average size of the openings on collection bag 22. Thus, smaller and intermediate sized particles can move more freely in and out of collection bag 22 than through filter 28, allowing for the collection of the larger size particles in collection bag 22.

The second end of tube 20 terminates in a flow limiter 26 that allows fluid (including any particulate material) to pass into collection bag 22, but not back out into tube 20. One example of a flow limiter 26 that can be used is a valve such as a check valve. Another flow limiter that can be used is a Penrose drain or other type of pliable length of tubing. Although a check valve may be more restrictive in preventing flow out of collection bag 22, the use of a pliable length of tubing may be beneficial in that the tubing would have no moving parts and is more cost efficient.

Figure 3:
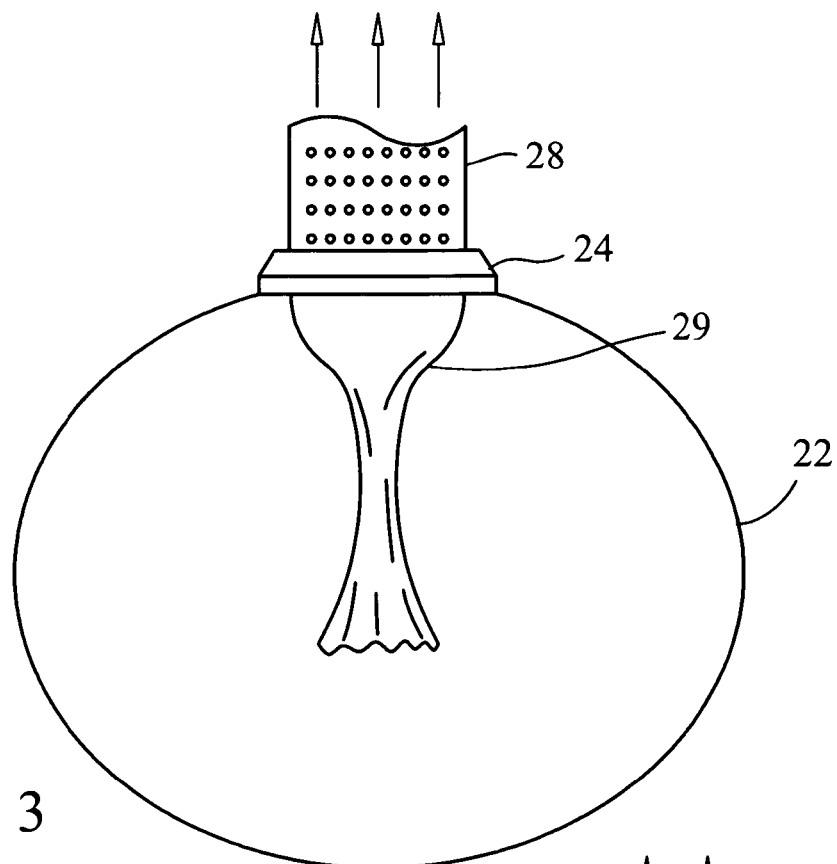
FIG. 3 is a sectional view of a flow limiter of the present invention.

Referring to FIG. 3, tube 20 includes a pliable tubing 29. When positive pressure is created within container 12 to force irrigation fluid from container 12 (for example, by squeezing pump bulb 14), a pressure differential is created between the irrigation fluid within pliable tubing 29 and the irrigation fluid surrounding pliable tubing 29. The irrigation fluid surrounding pliable tubing 29 has greater pressure then the irrigation fluid within pliable tubing 29, causing pliable tubing 29 to collapse within, effectively sealing off collection bag 22 and preventing the collected tissue and particulate material from re-entering the body cavity with the re-circulated irrigation fluid. Pliable tubing 29 can be provided with slits to facilitate the opening and closing of its lumen.

When the squeezing force is removed from pump bulb 14, creating negative pressure, the fluid is drawn from the body cavity into container 12 through tube 20. The drawing of the irrigation fluid through tube 20 into container 12 creates a pressure differential between the irrigation fluid within pliable tubing 29 and the irrigation fluid surrounding pliable tubing 29. The irrigation fluid within pliable tubing 29 has a greater pressure then the irrigation fluid surrounding pliable tubing 29 causing pliable tubing 29 to expand, providing access to collection bag 22 to collect and isolate the evacuated tissue and particulate material from the irrigation fluid.

Figures 4, 5:
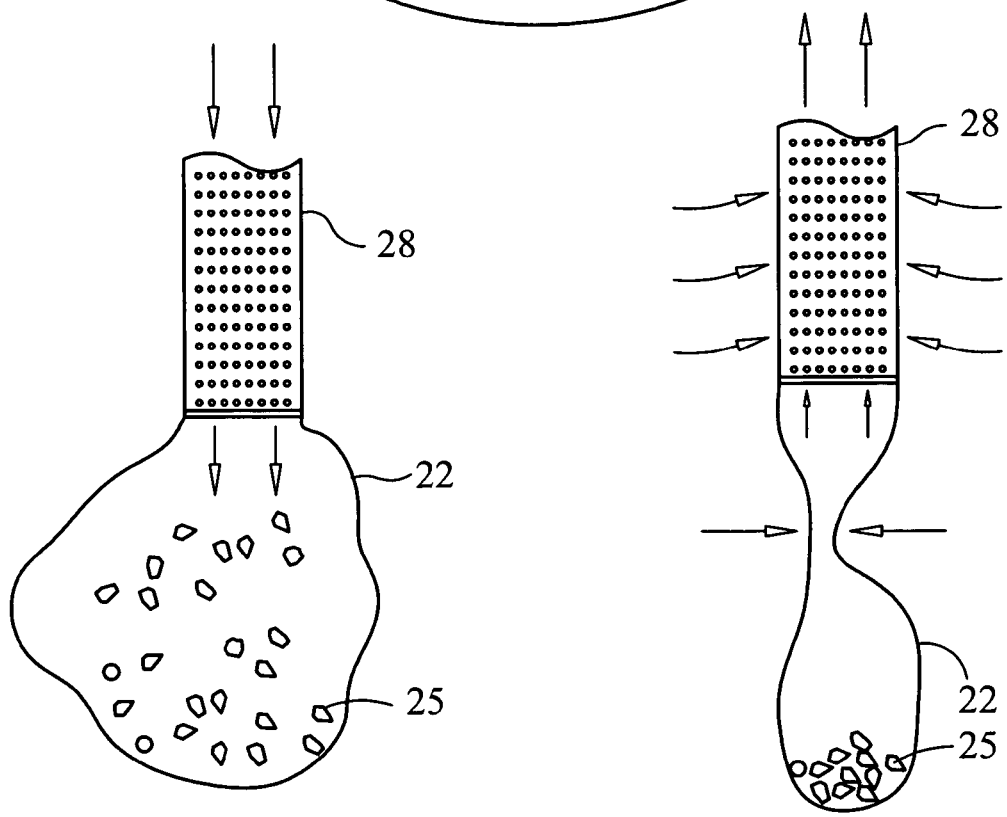
FIG. 4 is a schematic representation of the configuration of the mesh bag during fluid in flow.
FIG. 5 is a schematic representation of the configuration of the mesh bag during fluid out flow.

Collection bag 22 of the present invention can also be made of a pliable material (or as an alternate to pliable tubing). When the positive pressure is created to force irrigation fluid from container 12 as shown by the arrows of FIG. 5, a pressure differential is created between the irrigation fluid within collection bag 22 and the irrigation fluid surrounding collection bag 22. The irrigation fluid surrounding collection bag 22 has a greater pressure then the irrigation fluid within collection bag 22 causing collection bag 22 to collapse in on itself, preventing the collected tissue and particulate material 25 from re-entering the body cavity.

When the squeezing force is removed from pump bulb 14, creating negative pressure, the fluid is drawn into collection bag 22 through tube 20 as shown by the arrows of FIG. 4. The drawing of the irrigation fluid into collection bag 22 creates a pressure differential between the irrigation fluid within collection bag 22 and the irrigation fluid surrounding pliable collection bag 22. The irrigation fluid within collection bag 22 has a greater pressure then the irrigation fluid surrounding collection bag 22 causing collection bag 22 to expand, providing access to collection bag 22 to collect and isolate the evacuated tissue and particulate material 25 from the irrigation fluid.

In use, system 10 provides a system for irrigation and tissue evacuation and collection for any body cavity, such as the bladder. Container 12 can be filled with irrigation fluid and the entire system can be purged of air. As is well known in the art, purging can be accomplished, for example, by submerging the opened device in a fluid filled basin and repeatedly compressing the bulb, or by repeatedly dipping the nozzle of a closed device into irrigating fluid and aspirating with the bulb until full. An endoscope can be used to advance the fluid line to the body cavity (connected to tube 20) of interest.

By compressing pump bulb 14, irrigation fluid in container 12 is forced through filter 28 out through tube 20 which is connected to the body cavity via the fluid line. On relieving pressure on pump bulb 14, fluid is sucked back in from the body cavity through the fluid line and through tube 20. Particulate tissue and other material will be trapped in collection bag 22 while the rest of the fluid will refill container 12 and pump bulb 14. When desired, collection bag 22 can be disconnected and dropped in a specimen jar. In this way, separate specimens can be accurately collected and submitted without the potential for specimen tissue loss or mix-up. In this regard, container 12 or a portion thereof can be made transparent or translucent so that the turbidity of the fluid can be visually examined.

Figure 6:
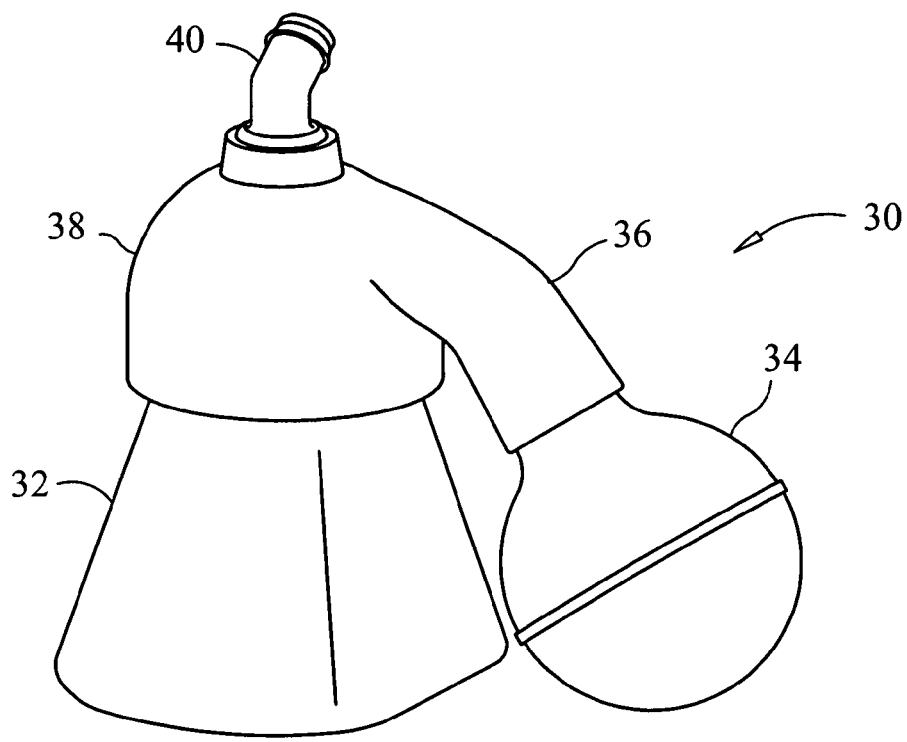
FIG. 6 is a perspective view of another embodiment of the system according to the present invention.
Figure 7:
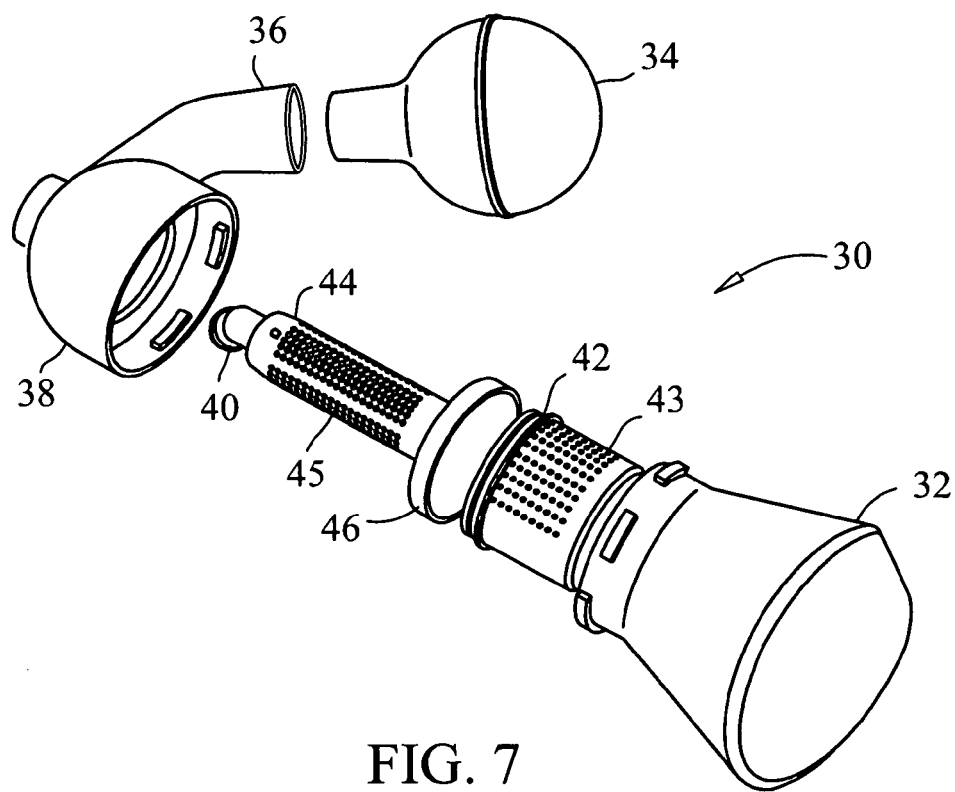
FIG. 7 is first exploded view of the system of FIG. 6.
Figure 8:
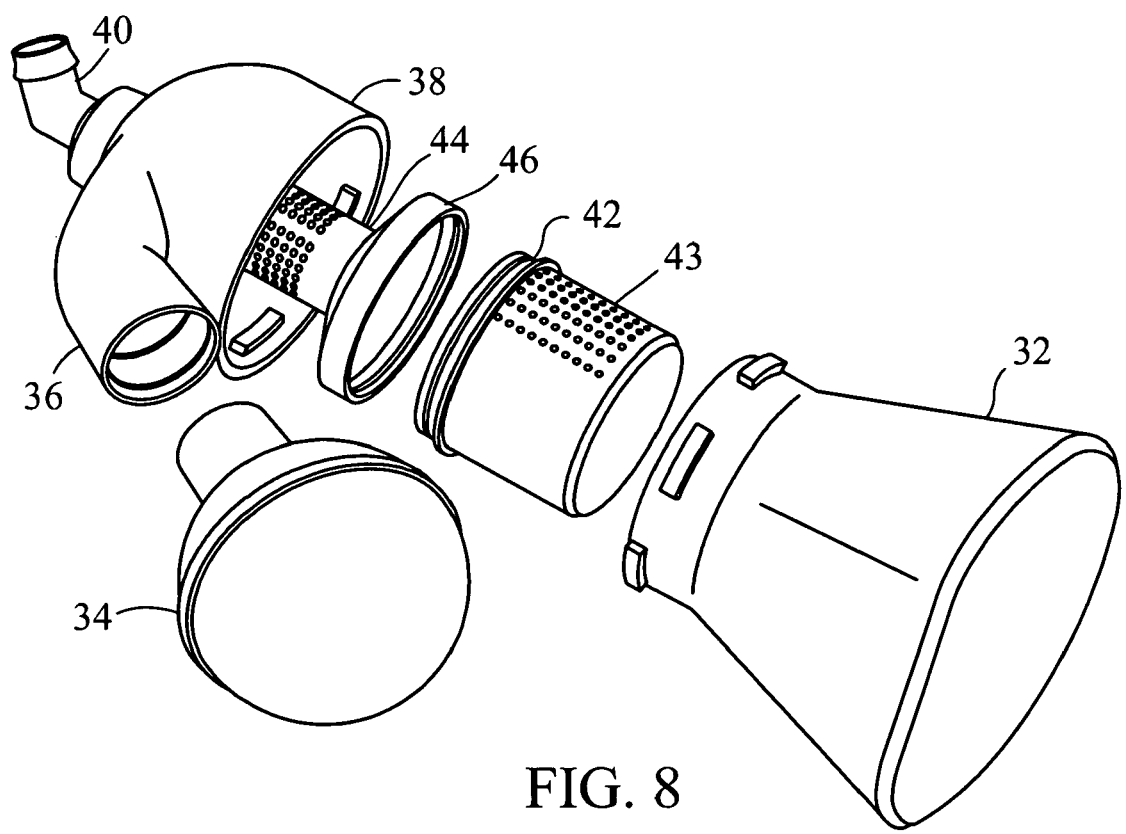
FIG. 8 is a second exploded view of the system of FIG. 6.

Referring to FIGS. 6–8, another embodiment of an irrigation and tissue evacuation and collection system 30 according to the present invention is shown. In general, most of the structure and function of system 30 is like or comparable to the structure of system 10 and, accordingly the same name and an analogous reference numeral are used for like components and discussion of those like components is not believed necessary.

System 30 includes a container 32 for holding irrigation fluid. A pump bulb 34 is coupled to a removable cap 38 via a pump conduit 36. Alternatively, pump conduit 36 is attached to container 32. In contrast to conduit 16, conduit 36 extends downwardly at a non-orthogonal angle from cap 38. In addition to improved feel and handling, this configuration also facilitates purging of air with pump bulb 34.

A tube 40 provides the pathway for the irrigation fluid into and out of container 32. One end of tube 40 is removably coupled to a collection basket 42 via a connecting tube 44. As collection basket 42 can be made of a mesh type material or be perforated to have an array of openings 43, different baskets having a range of mesh size openings can be used to suit a particular application. If desired, collection basket 42 can be made of a rigid material, such as a suitable polymer.

Connecting tube 44 flares outwardly to form a flange 46. Although flange 46 is shown as threaded to mate with threads on collection basket 42, other coupling mechanisms could be used. Like collection basket 42, connecting tube 44 is provided with pores 45 to restrict throughflow of particulate material above a certain size. As was the case for system 10, the relative sizes (average cross sectional areas) of openings 43 and pores 45 can be varied to suit a particular application.

Connecting tube 44 is configured and dimensioned and arranged with respect to conduit 36 such that the portion of connecting tube 44 located within and in close proximity to cap 38 experiences higher turbulence and flow compared to other portions (i.e. portions closer to flange 46). As a result, fluid near the base of container 32 in the vicinity of the bottom of collection basket 42 remains substantially undisturbed and substantially free of turbulent flow. This tends to allow material to settle in collection basket 42, while still providing for adequate circulation of fluid.

Figure 9:
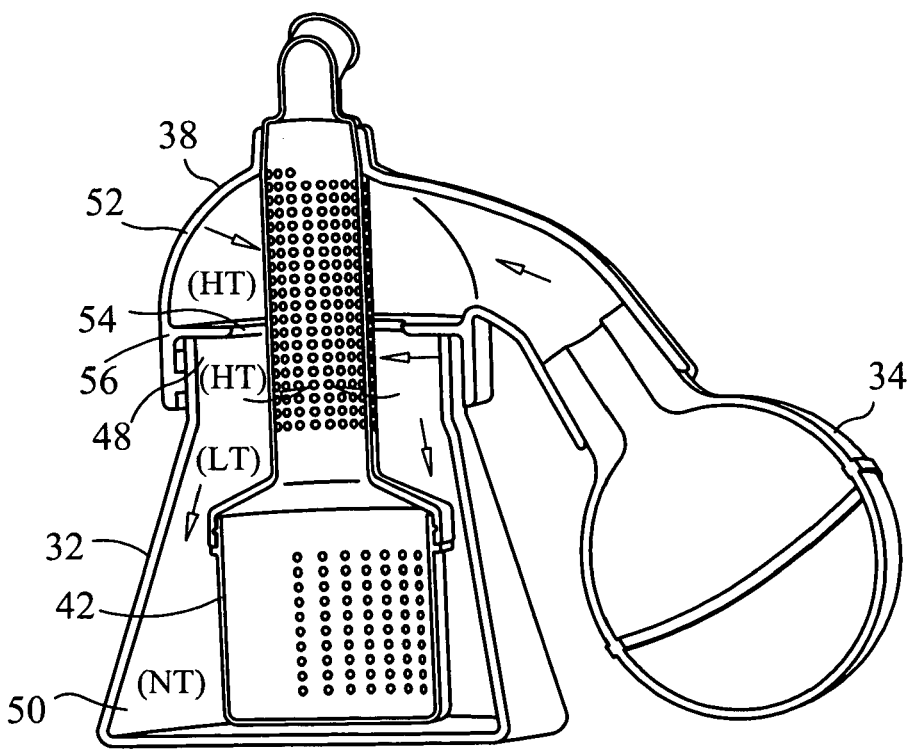
FIG. 9 is a cross-sectional view of the system of FIG. 6 showing fluid flow patterns.

Referring to FIG. 9, container 32 includes an upper portion 48 and a lower portion 50. Container 32 may be configured and dimensioned such that the cross sectional area of lower portion 50 is larger then the cross sectional area of upper portion 48. For example and as generally shown, container 32 can have a substantially frusto-conical shape. The configuration and dimension of container 32 disperses the turbulent flow as the fluid travels from upper portion 48 to lower portion 50 of container 32. As described above, by compressing pump bulb 34, irrigation fluid is forced into container 32, creating highly turbulent flow (HT) in upper portion 48 of container 32. As the irrigation fluid is forced into lower portion 50 of container 32, the increasing cross section of container 32 disperses the turbulent flow, creating a lower turbulent flow (LT). As a result, fluid in lower portion 50 of container 32, in the vicinity of the bottom of collection basket 42, remains substantially undisturbed and substantially free of turbulent flow (NT). This tends to allow material to settle in collection basket 42, while still providing for adequate circulation of fluid.

In one embodiment, removable cap 38 defines a cap interior 52. Cap interior 52 is removably attached to container 32 and defines a fluid interface 54 between upper portion 48 of container 32 and cap interior 52. By compressing pump bulb 34, irrigation fluid is forced into cap interior 52, creating highly turbulent flow (HT) in cap interior 52 and upper portion 48 of container 32. As the irrigation fluid is forced into lower portion 50 of container 32, the increasing distance, flow restriction and, in some embodiments, the increasing cross sectional area of container 32 disperses the turbulent flow, creating a lower turbulent flow (LT). As a result, fluid in lower portion 50 of container 32, in the vicinity of the bottom of collection basket 42, remains substantially undisturbed and substantially free of turbulent flow (NT). This tends to allow material to settle in collection basket 42, while still providing for adequate circulation of fluid.

System 30 optionally includes a flow restrictor 56, which partially segregates cap interior 52 from upper portion 48 of container 32. Flow restrictor 56 can be part of removable cap 38. For example, flow restrictor 56 can be a lip circumferentially extending from cap 38 to partially segregate cap interior 52 from upper portion 48 of the container 32. Alternatively, flow restrictor 52 can be positioned within upper portion 48 of container 32.

Flow restrictor 56 acts to decrease the cross sectional area of fluid interface 54 between cap interior 52 and upper portion 48 of container 32. The restricted fluid interface 54 acts to limit the propagation of the highly turbulent flow (HT), caused by compressing pump bulb 34, from cap interior 52 into lower portion 50 of container 32.

As noted above, compressing pump bulb 34 creates highly turbulent flow (HT) in cap interior 52. As the irrigation fluid is forced into upper portion 48 of container 32, the restricted fluid interface 54 limits the propagation of the highly turbulent flow into upper portion 48 of container 32. Furthermore, the increasing cross sectional area of container 32 further disperses the remaining turbulent flow, creating a lower turbulent flow (LT). As a result, fluid in lower portion 50 of container 32, in the vicinity of the bottom of collection basket 42, remains substantially undisturbed and substantially free of turbulent flow (NT). This tends to allow material to settle in collection basket 42, while still providing for adequate circulation of fluid.

Figure 10:
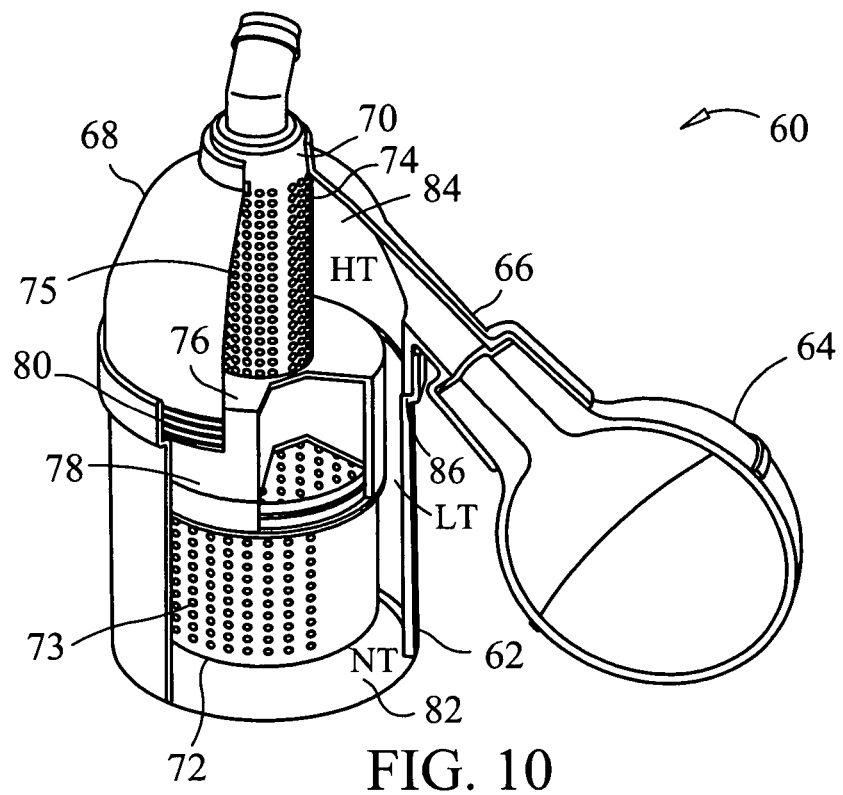
FIG. 10 is a perspective view of another embodiment of the system according to the present invention.

Referring to FIG. 10, another embodiment of an irrigation and tissue evacuation and collection system 60 according to the present invention is shown. In general, most of the structure and function of system 60 is like or comparable to the structure of the prior systems and, accordingly the same name and an analogous reference numeral are used for like components and discussion of those like components is not believed necessary.

System 60 includes a container 62 for holding irrigation fluid. A pump bulb 64 is coupled to a removable cap 68 via a pump conduit 66. Alternatively, pump conduit 66 is attached to container 62. In contrast to conduit 16, conduit 66 extends downwardly at an angle from cap 68. In addition to improved feel and handling, this configuration also facilitates purging of air with pump bulb 64. Pump bulb 64 is frictional connected to pump conduit 66, by inserting a portion of pump bulb 64 in conduit 66. Alternatively, pump bulb 64 is threadably connected to pump conduit 66.

A tube 70 provides the pathway for the irrigation fluid into and out of container 62. One end of tube 70 is removably coupled to a collection basket 72 via a connecting tube 74. As collection basket 72 can be made of a mesh type material or be perforated to have an array of openings 73, different baskets having a range of mesh size openings can be used to suit a particular application. If desired, collection basket 72 can be made of a rigid material, such as a suitable polymer.

Connecting tube 74 flares outwardly to form a flange 76. A flange skirt 78 extends from the flange 76. Although flange skirt 78 is shown as threaded to mate with threads on collection basket 72, other coupling mechanisms could be used. Like collection basket 72, connecting tube 74 is provided with pores 75 to restrict throughflow of particulate material above a certain size. As was the case for the prior systems the relative sizes (average cross sectional areas) of openings 73 and pores 75 can be varied to suit a particular application.

Connecting tube 74 is configured and dimensioned and arranged with respect to conduit 66 such that the portion of connecting tube 74 located within and in close proximity to cap 68 experiences higher turbulence and flow compared to other portions (i.e. portions closer to flange 76). As a result, fluid near the base of container 62 in the vicinity of the bottom of collection basket 72 remains substantially undisturbed and substantially free of turbulent flow. This tends to allow material to settle in collection basket 72, while still providing for adequate circulation of fluid.

The container 62 includes an upper portion 80 and a lower portion 82. The configuration and dimension of container 62, flange 76, and the flange skirt 78 limit the propagation of the turbulent flow as the fluid travels from upper portion 80 to lower portion 82 of container 62. As described above, by compressing pump bulb 64, irrigation fluid is forced into container 62, creating highly turbulent flow (HT) in upper portion 80 of container 62. As the irrigation fluid is forced into lower portion 82 of container 62, the restricted spacing between the inner wall of the container 62 and the flange 76 and the flange skirt limit the propagation of the turbulent flow, creating a lower turbulent flow (LT). Turbulence is also reduced in lower portion 82 by increasing the distance from pump conduit 66 (i.e. increasing the length of container 62). As a result, fluid in lower portion 82 of container 62, in the vicinity of the collection basket 72 (and in particular near the bottom of collection basket 72), remains substantially undisturbed and substantially free of turbulent flow (NT). This tends to allow material to settle in collection basket 72, while still providing for adequate circulation of fluid.

In one embodiment, removable cap 68 defines a cap interior 84. Cap interior 84 is removably attached to container 62 and defines a fluid interface 86 between upper portion 80 of container 62 and cap interior 84. By compressing pump bulb 64, irrigation fluid is forced into cap interior 84, creating highly turbulent flow (HT) in cap interior 84 and upper portion 80 of container 62. As the irrigation fluid is forced into lower portion 82 of container 62, the increasing distance and flow restriction disperses the turbulent flow, creating a lower turbulent flow (LT). As a result, fluid in lower portion 82 of container 62, in the vicinity of the collection basket 72 (and in particular near the bottom of collection basket 72), remains substantially undisturbed and substantially free of turbulent flow (NT). This tends to allow material to settle in collection basket 72, while still providing for adequate circulation of fluid.

Figure 11:
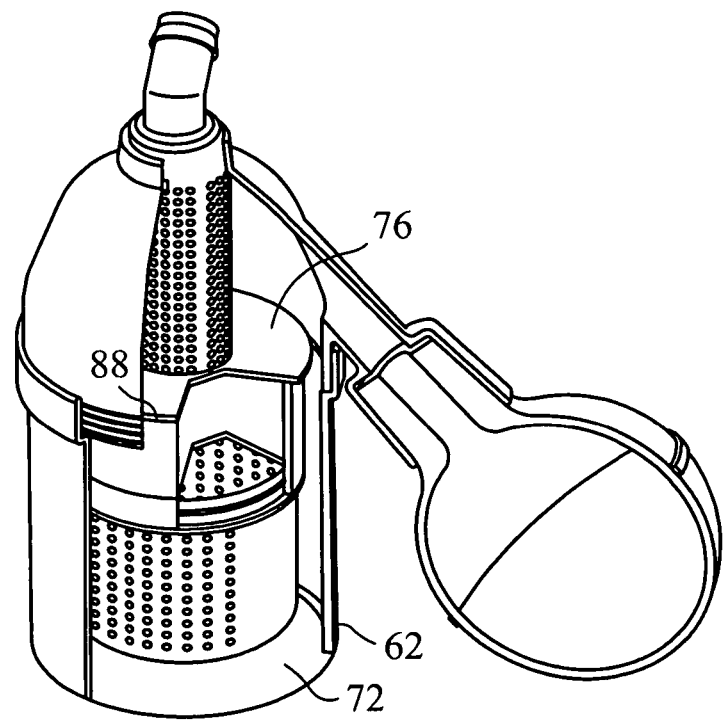
FIG. 11 is an alternative embodiment of the system of FIG. 10.

As shown in FIG. 11, the flange 76 optionally includes a lip portion 88, radially extending from the flange 76. The lip portion 88 acts to further limit the propagation of the turbulent flow to the bottom portion of the container 72.

Figure 12:
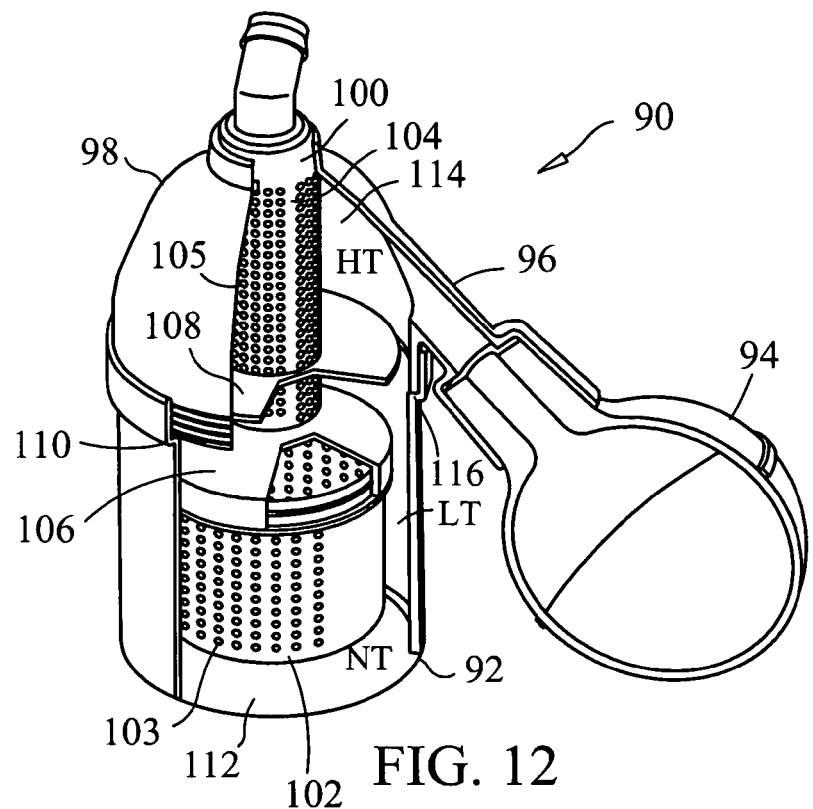
FIG. 12 is a perspective view of another embodiment of the system according to the present invention.

Referring to FIG. 12, another embodiment of an irrigation and tissue evacuation and collection system 90 according to the present invention is shown. In general, most of the structure and function of system 90 is like or comparable to the structure of systems 10, 30, and 60 and, accordingly the same name and an analogous reference numeral are used for like components and discussion of those like components is not believed necessary.

System 90 includes a container 92 for holding irrigation fluid. A pump bulb 94 is coupled to a removable cap 98 via a pump conduit 96. Alternatively, pump conduit 96 is attached to container 92.

A tube 100 provides the pathway for the irrigation fluid into and out of container 92. One end of tube 100 is removably coupled to a collection basket 102 via a connecting tube 104. As collection basket 102 can be made of a mesh type material or be perforated to have an array of openings 103, different baskets having a range of mesh size openings can be used to suit a particular application. If desired, collection basket 102 can be made of a rigid material, such as a suitable polymer.

Connecting tube 104 flares outwardly to form a flange 106. Although flange 106 is shown as threaded to mate with threads on collection basket 102, other coupling mechanisms could be used. Like collection basket 102, connecting tube 104 is provided with pores 105 to restrict throughflow of particulate material above a certain size. A restrictor plate 108 radially extends from connection tube 104 and is interposed between the flange 106 and the cap 98.

Connecting tube 104, flange 106, and restrictor plate 108 are configured, dimensioned and arranged with respect to conduit 96 such that the portion of connecting tube 104 located within and in close proximity to cap 98 experiences higher turbulence and flow compared to other portions (i.e. portions closer to flange 106). As a result, fluid near the base of container 92 in the vicinity of the collection basket 102 (and in particular near the bottom of collection basket 102) remains substantially undisturbed and substantially free of turbulent flow. In particular, restrictor plate 108 acts like a shield, directing fluid from pump conduit 96 toward tube 100. The combined effect of these features tends to allow material to settle in collection basket 102, while still providing for adequate circulation of fluid.

The container 92 includes an upper portion 110 and a lower portion 112. The configuration and dimension of container 92, flange 106, and the restrictor plate 108 limit the propagation of the turbulent flow as the fluid travels from upper portion 110 to lower portion 112 of container 92. As described above, by compressing pump bulb 94, irrigation fluid is forced into container 92, creating highly turbulent flow (HT) in upper portion 110 of container 92. As the irrigation fluid is forced into lower portion 112 of container 92, the restrictor plate 108 and the flange 106 limit the propagation of the turbulent flow, creating a lower turbulent flow (LT). As a result, fluid in lower portion 112 of container 92, in the vicinity of the collection basket 102 (and in particular near the bottom of collection basket 102), remains substantially undisturbed and substantially free of turbulent flow (NT). This tends to allow material to settle in collection basket 102, while still providing for adequate circulation of fluid.

In one embodiment, removable cap 98 defines a cap interior 114. Cap interior 114 is removably attached to container 92 and defines a fluid interface 116 between upper portion 110 of container 92 and cap interior 114. By compressing pump bulb 94, irrigation fluid is forced into cap interior 114, creating highly turbulent flow (HT) in cap interior 114 and upper portion 110 of container 92. As the irrigation fluid is forced into lower portion 112 of container 92, the increasing distance and flow restriction disperses the turbulent flow, creating a lower turbulent flow (LT). As a result, fluid in lower portion 112 of container 92, in the vicinity of the collection basket 102 (and in particular near the bottom of collection basket 102), remains substantially undisturbed and substantially free of turbulent flow (NT). This tends to allow material to settle in collection basket 102, while still providing for adequate circulation of fluid.

Figure 13:
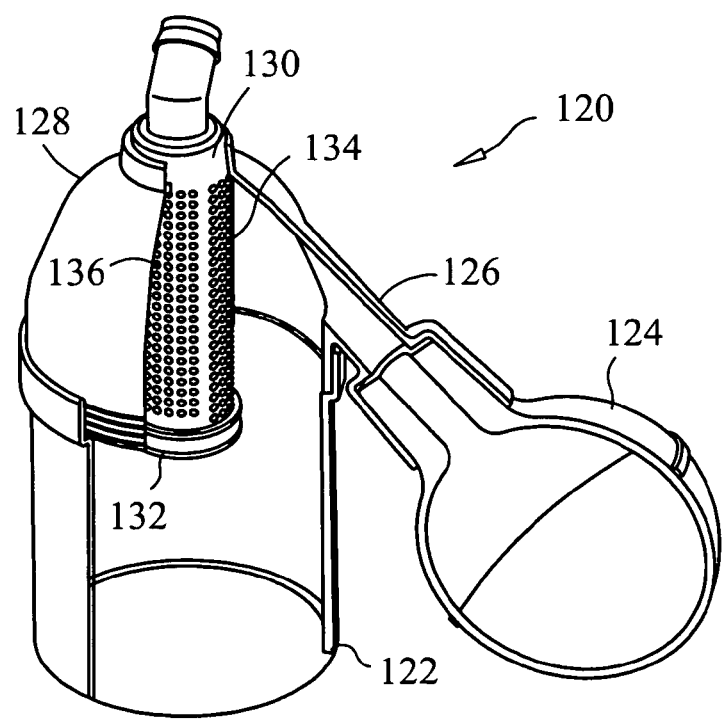
FIG. 13 is a perspective view of another embodiment of the system according to the present invention.

Referring to FIG. 13, another embodiment of an irrigation and tissue evacuation and collection system 120 according to the present invention is shown. In general, most of the structure and function of system 120 is like or comparable to the structure of the prior systems and, accordingly, the same name and an analogous reference numeral are used for like components and discussion of those like components is not believed necessary.

Figure 15:
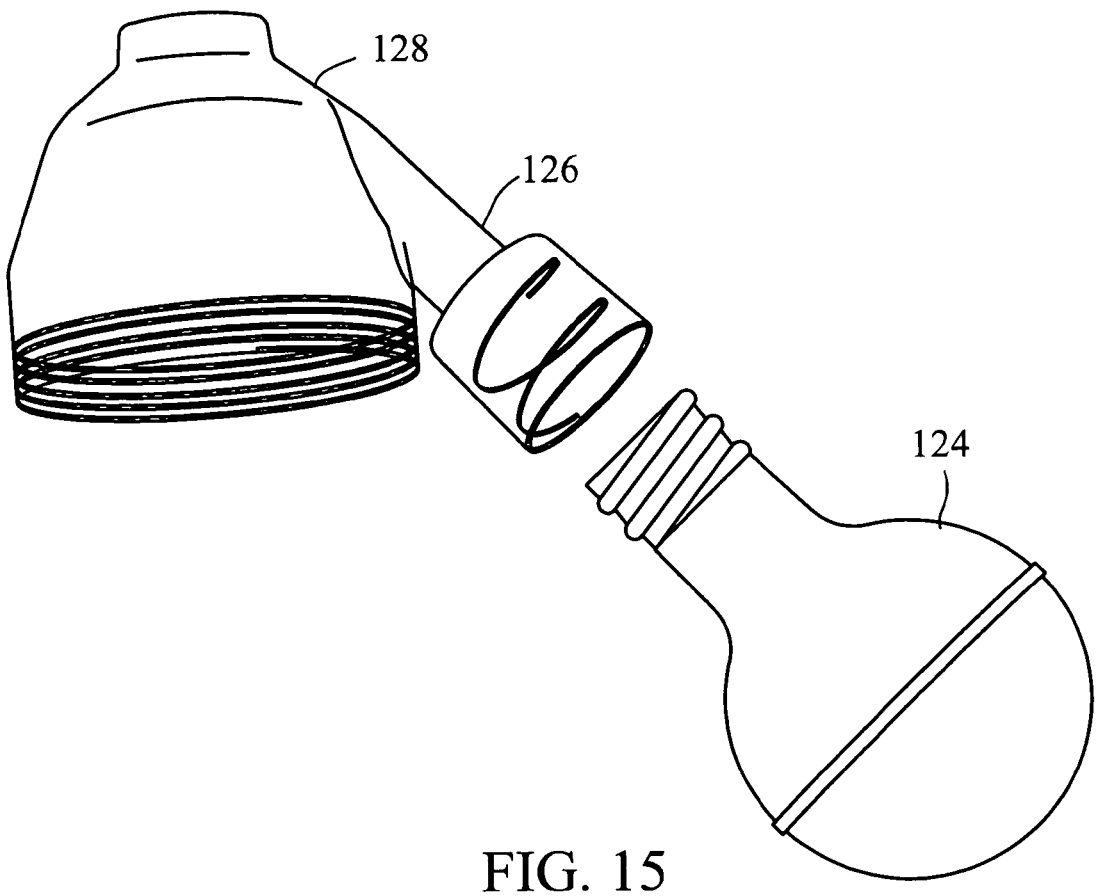
FIG. 15 is an exploded view showing a pump bulb threadably coupled to a pump conduit.

System 120 includes a container 122 for holding irrigation fluid. A pump bulb 124 is coupled to a removable cap 128 via a pump conduit 126. Alternatively, pump conduit 126 is attached to container 122. As has previously been discussed and is shown in FIG. 15, pump bulb 124 is threadably connected to pump conduit 126.

A tube 130 provides the pathway for the irrigation fluid into and out of container 122. A lower end portion 132 of the tube 130 is removably coupled to a collection bag (not shown) via a connecting tube 134. As the collection bag can be made of a mesh type material or be perforated to have an array of openings, different bags having a range of mesh size openings can be used to suit a particular application.

Like the collection bag, connecting tube 134 is provided with pores 136 to restrict throughflow of particulate material above a certain size. As was the case for the prior systems, the relative sizes (average cross sectional areas) of the collection bag openings and pores 136 can be varied to suit a particular application.

Connecting tube 134 is configured, dimensioned and arranged with respect to conduit 126 such that the portion of connecting tube 134 located within and in close proximity to cap 128 experiences higher turbulence and flow compared to other portions. As a result, fluid near the base of container 122 in the vicinity of the collection bag (and in particular near the bottom of the collection bag) remains substantially undisturbed and substantially free of turbulent flow. This tends to allow material to settle in collection bag, while still providing for adequate circulation of fluid.

Figure 14:
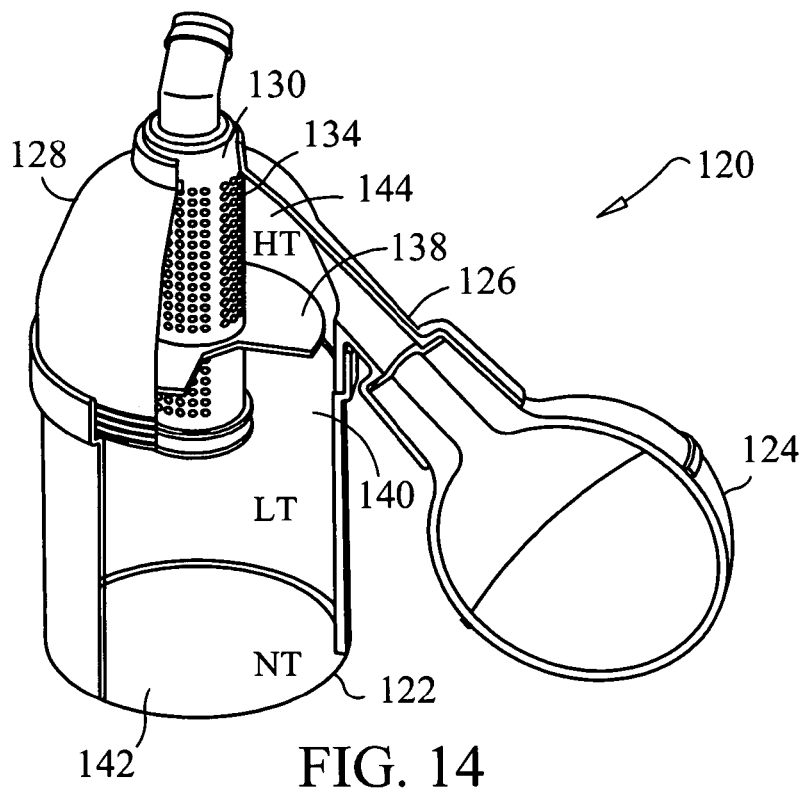
FIG. 14 is an alternative embodiment of the system of FIG. 13.

Referring to FIG. 14, connecting tube 134 includes a restrictor plate 138 radially extending out there from. Restrictor plate 138 is interposed between the lower end portion 134 of tube 130 and cap 128, and acts like a shield directing fluid from pump conduit 126 toward tube 130. If desired, restrictor plate 138 can snugly fit against the edge of cap 128 to be fluid-tight, thereby serving as a bulkhead so that fluid must pass through connecting tube 134 to reach the lower section of container 122.

Container 122 includes an upper portion 140 and a lower portion 142. The configuration and dimension of container 122 and restrictor plate 138 limits the propagation of the turbulent flow as the fluid travels from upper portion 140 to lower portion 142 of container 122. As described above, by compressing pump bulb 124, irrigation fluid is forced into container 122, creating highly turbulent flow (HT) in upper portion 140 of container 122. As the irrigation fluid is forced into lower portion 142 of container 122, restrictor plate 138 limits the propagation of the turbulent flow, creating a lower turbulent flow (LT). As a result, fluid in lower portion 142 of container 122, in the vicinity of the collection bag (and in particular near the bottom of the collection bag), remains substantially undisturbed and substantially free of turbulent flow (NT). This tends to allow material to settle in the collection bag, while still providing for adequate circulation of fluid.

In one embodiment, removable cap 128 defines a cap interior 144. Cap interior 144 is removably attached to container 122 and defines a fluid interface 146 between upper portion 140 of container 122 and cap interior 144. By compressing pump bulb 124, irrigation fluid is forced into cap interior 144, creating highly turbulent flow (HT) in cap interior 144 and upper portion 140 of container 122. As the irrigation fluid is forced into lower portion 142 of container 122, the increasing distance and flow restriction disperses the turbulent flow, creating a lower turbulent flow (LT). As a result, fluid in lower portion 142 of container 122, in the vicinity of the collection bag (and in particular near the bottom of the collection bag), remains substantially undisturbed and substantially free of turbulent flow (NT). This tends to allow material to settle in collection bag, while still providing for adequate circulation of fluid.

All references cited herein are expressly incorporated by reference in their entirety. In addition, unless mention was made above to the contrary, it should be noted that all of the accompanying drawings are not to scale.

There are many different features to the present invention and it is contemplated that these features may be used together or separately. Thus, the invention should not be limited to any particular combination of features or to a particular application of the invention. For example, although flow limiter 26 is discussed as part of system 10, it is also contemplated by the present invention that flow limiter 26, or a similar mechanism, could be used in conjunction with any of the other embodiments. Further, it should be understood that variations and modifications within the spirit and scope of the invention might occur to those skilled in the art to which the invention pertains. Accordingly, all expedient modifications readily attainable by one versed in the art from the disclosure set forth herein that are within scope and spirit of the present invention are to be included as further embodiments of the present invention. The scope of the present invention is accordingly defined as set forth in the appended claims.

What is claimed is:

1. A medical irrigation and tissue collection system for introducing fluid into and withdrawing fluid from a body cavity via a fluid line, the system comprising:
   a container having an interior for holding fluid;
   a pump bulb in fluid communication with the container;
   a tube having a first end portion connected with the fluid line and a second end portion in fluid communication with the interior of the container; and
   a collection receptacle for collecting particulate material, the collection receptacle located within the interior of the container and removably connected to the second end portion of the tube;
   wherein the collection receptacle is provided with a plurality of openings allowing the passage of fluid and particulate material smaller than a predetermined size.

2. The medical irrigation and tissue collection system of claim 1 wherein the second end portion has a perforated section with a plurality of pores allowing the passage of fluid and particulate material of a given size.

3. The medical irrigation and tissue collection system of claim 2 wherein the plurality of openings has an average opening size and the plurality of pores has an average pore size, the average pore size area being smaller than the average opening size.

4. The medical irrigation and tissue collection system of claim 2 further comprising a one-way valve operatively associated with the tube allowing fluid and particulate material to flow through the tube and pass into the collection receptacle.

5. The medical irrigation and tissue collection system of claim 4 wherein the one-way valve is coupled to the second end portion of the tube and includes a length of tubing collapsible under a pressure differential generated by the pump bulb.

6. A medical irrigation and tissue collection system for introducing fluid into and withdrawing fluid from a body cavity via a fluid line, the system comprising:
   a container having an interior for holding fluid;
   a pump bulb in fluid communication with the container;
   a tube having a first end portion connected with the fluid line and a second end portion in fluid communication with the interior of the container;
   a collection receptacle for collecting particulate material the collection receptacle located within the interior of the container and removably connected to the second end portion of the tube; and
   a one-way valve operatively associated with the tube allowing fluid and particulate material to flow through the tube and pass into the collection receptacle;
   wherein the collection receptacle is provided with a plurality of openings allowing the passage of fluid and particulate material smaller than a predetermined size;
   wherein the second end portion has perforated section with a plurality of pores allowing the passage of fluid and particulate material of a given size;
   wherein the one-way valve is coupled to the second end portion of the tube and includes a length of tubing collapsible under a pressure differential generated by the pump bulb; and
   wherein the collection receptacle is a mesh bag.

7. The medical irrigation and tissue collection system of claim 6 wherein the mesh bag is collapsible under a pressure differential generated by the pump bulb.

8. A medical irrigation and tissue collection system for introducing fluid into and withdrawing fluid from a body cavity via a fluid line, the system comprising:
   a container having an interior for holding fluid;
   a pump bulb in fluid communication with the container;
   a tube having a first end portion connected with the fluid line and a second end portion in fluid communication with the interior of the container; and
   a collection receptacle for collecting particulate material, the collection receptacle located within the interior of the container and removably connected to the second end portion of the tube;
   wherein the collection receptacle is provided with a plurality of openings allowing the passage of fluid and particulate material smaller than a predetermined size;
   wherein the second end portion has a perforated section with a plurality of pores allowing the passage of fluid and particulate material of a given size; and
   wherein the collection receptacle is a mesh bag.

9. The medical irrigation and tissue collection system of claim 8 wherein the mesh bag is collapsible under a pressure differential generated by the pump bulb.

10. The medical irrigation and tissue collection system of claim 9 further comprising a flow restrictor positioned above the mesh bag.

11. The medical irrigation and tissue collection system of claim 10 wherein the flow restrictor is a restrictor plate radially extending from the tube.

12. The medical irrigation and tissue collection system of claim 2 further comprising a cap removably coupled to the container.

13. The medical irrigation arid tissue collection system of claim 12 further comprising a pump conduit having a first end portion extending from the cap and a second end portion coupled to the pump bulb.

14. The medical irrigation and tissue collection system of claim 13 wherein the pump bulb is threadably mounted to the pump conduit.

15. The medical irrigation and tissue collection system of claim 13 wherein the pump conduit extends downwardly from the cap.

16. The medical irrigation and tissue collection system of claim 15 wherein the collection receptacle is a basket made of a rigid polymeric material.

17. The medical irrigation and tissue collection system of claim 13 wherein the container has upper and lower portions with the cap removably coupled to the upper portion proximate an upper edge thereof.

18. The medical irrigation and tissue collection system of claim 17 wherein the collection receptacle is located within the lower portion of the container and extends proximate a bottom thereof.

19. A medical irrigation and tissue collection system for introducing fluid into and withdrawing fluid from a body cavity via a fluid line, the system comprising:
   a container having an interior for holding fluid;
   a pump bulb in fluid communication with the container;
   a tube having a first end portion connected with the fluid line and a second end portion in fluid communication with the interior of the container;
   a collection receptacle for collecting particulate material, the collection receptacle located within the interior of the container and removably connected to the second end portion of the tube;
   a cap removably coupled to the container; and
   a pump conduit having a first end portion extending from the cap and a second end portion coupled to the pump bulb;

wherein the collection receptacle is provided with a plurality of openings allowing the passage of fluid and particulate material smaller than a predetermined size;

wherein the second end portion has a perforated section with a plurality of pores allowing the passage of fluid and articulate material of a given size;

wherein the container has upper and lower portions with the cap removably coupled to the upper portion;

wherein the collection receptacle is located within the lower portion of the container and wherein the upper and lower portions of the container are configured and dimensioned such that turbulent flow resulting from pressure generated by compressing the pump bulb is higher in the upper portion of the container compared to the lower portion of the container.

20. The medical irrigation and tissue collection system of claim 19 wherein the collection receptacle is a basket made of a rigid polymeric material.

21. The medical irrigation and tissue collection system of claim 20 wherein a bottom of the basket experiences substantially no turbulent flow from the pressure generated by compressing the pump bulb.

22. A medical irrigation and tissue collection system for introducing fluid into and withdrawing fluid from a body cavity via a fluid line, the system comprising:
a container having an interior for holding fluid;
a pump bulb in fluid communication with the container;
a tube having a first end portion connected with the fluid line and a second end portion in fluid communication with the interior of the container;
a collection receptacle for collecting particulate material, the collection receptacle located within the interior of the container and removably connected to the second end portion of the tube;
a cap removably coupled to the container; and
a pump conduit having a first end portion extending from the cap and a second end portion coupled to the pump bulb;
wherein the collection receptacle is provided with a plurality of openings allowing the passage of fluid and particulate material smaller than a predetermined size;
wherein the second end portion has a perforated section with a plurality of pores allowing the passage of fluid and particulate material of a given size;
wherein the container has upper and lower portions wit the cap removably coupled to the upper portion; and
wherein the cap defines a cap interior and turbulent flow resulting from the pressure generated by compressing the pump bulb is substantially limited to the cap interior.

23. The medical irrigation and tissue collection system of claim 22 further comprising a flow restrictor located between the cap interior and the upper portion of the container.

24. The medical irrigation and tissue collection system of claim 23 wherein the flow restrictor is a lipped portion of the cap.

25. The medical irrigation and tissue system of claim 23 wherein the flow restrictor is a restrictor plate radially extending from the tube.

26. A medical irrigation and tissue collection system for introducing fluid into and withdrawing fluid from a body cavity via a fluid line, the system comprising:
a container defining a container interior for holding a fluid;
a pump bulb in fluid communication with the container interior;
a tube having a first end portion connected with the fluid line and a second end portion positioned in the container interior; and
a collection receptacle positioned in the container interior and connected to the second end portion of the tube, the collection receptacle including a plurality of openings allowing passage of the fluid and particulate material smaller than a predetermined size therethrough;
wherein the container interior has upper and lower portions, the upper and lower portions configured and dimensioned and arranged with respect to the pump bulb such that turbulent flow generated by the pump bulb is substantially limited to the upper portion and the lower portion is substantially free of turbulence.

27. The medical irrigation and tissue collection system of claim 26 further comprising a pump conduit having a first end portion extending from the container in fluid communication with upper portion of the container interior and a second end portion coupled to the pump bulb.

28. The medical irrigation and tissue collection system of claim 27, wherein the pump conduit is configured to position the pump bulb below the upper portion of the container interior.

29. The medical irrigation and tissue collection system of claim 26 further comprising a cap removably coupled to the container.

30. The medical irrigation and tissue collection system of claim 29, wherein the tube includes a perforated section having a plurality of pores allowing the passage of the fluid and particulate material of a given size therethrough.

31. The medical irrigation and tissue collection system of claim 30 further comprising a flow restrictor located between the cap interior and the upper portion of the container interior.

32. The medical irrigation and tissue collection system of claim 31 wherein the flow restrictor is a lipped portion of the cap.

33. The medical irrigation and tissue collection system of claim 31 wherein the flow restrictor is a restrictor plate radially extending from the tube.

34. A method of collecting tissue and particulate material from a body cavity in a patient, the method comprising:
positioning a medical irrigation and tissue collection device in fluid communication with the body cavity;
injecting an irrigation fluid from the medical irrigation and tissue collection device into the body cavity;
evacuating the irrigation fluid from the body cavity into the medical irrigation and tissue collection device, wherein the evacuated irrigation fluid includes tissue and particulate material from the body cavity; and
filtering the evacuated irrigation fluid to isolate tissue and particulate material within the irrigation fluid such that the tissue and particulate material is collected in a collection receptacle located within the medical irrigation and tissue collection device.

35. A method of collecting tissue and particulate material from a body cavity in a patient, the method comprising:
positioning a medical irrigation and tissue collection device in fluid communication with the body cavity;
injecting an irrigation fluid from the medical irrigation and tissue collection device into the body cavity;
evacuating the irrigation fluid from the body cavity into the medical irrigation and tissue collection device, wherein the evacuated irrigation fluid includes tissue and particulate material from the body cavity; and
filtering the evacuated irrigation fluid to isolate tissue and particulate material within the irrigation fluid such that the tissue and particulate material is collected in a collection receptacle located within the medical irrigation and tissue collection device;

wherein injecting an irrigation fluid from the medical irrigation and tissue collection device into the body cavity comprises creating a positive pressure within the irrigation and tissue collection device into the body cavity, including creating a turbulent flow in an upper portion of the medical irrigation and tissue collection device, while maintaining a substantially turbulent free flow in a lower portion of the medical irrigation and tissue collection device.

36. The method of claim 34 wherein filtering the evacuated irrigation fluid to isolate tissue and particulate material within the irrigation fluid includes collecting tissue and particulate material in the lower portion of the medical irrigation and tissue collection device.

37. The method of claim 34, further comprising:
purging air from the medical irrigation and tissue collection device.

38. The method of claim 35, further comprising:
purging air from the medical irrigation and tissue collection device.

39. A system for medical irrigation and tissue collection by introducing fluid into and withdrawing fluid from a body cavity, the system comprising:
a container having a container interior;
a cap demountably coupled to the container;
a portion for connection to a fluid line communicating with the body cavity;
a pump conduit;
a pump bulb demountably coupled to the pump conduit;
a receptacle disposed in the container interior, the receptacle having a first set of openings of a first size for permitting movement of fluid and particulate therethrough; and
a tube demountably coupled to the receptacle, the tube having a second set of openings of a second size for permitting movement of fluid and particulate therethrough.

40. The system of claim 39, wherein the tube comprises a flange, the tube being demountably coupled to the receptacle at the flange.

41. The system of claim 39, wherein the pump conduit is oriented non-orthogonally with respect to the tube.

42. The system of claim 39, wherein the tube is demountably coupled to the cap.

43. The system of claim 39, wherein the pump conduit extends from the cap and has a conduit opening disposed proximate the portion for connection to a fluid line.

44. The system of claim 43, wherein the tube extends within the cap proximate the pump conduit.

45. The system of claim 44, wherein the second set of openings are disposed proximate the conduit opening.

46. The system of claim 39, wherein a first end of the tube is coupled to the cap.

47. The system of claim 39, wherein a first end of the tube abuts the cap.

48. The system of claim 39, wherein the first size is different from the second size.

49. The system of claim 39, wherein the pump conduit extends from the cap and comprises a flared portion for coupling to the pump bulb.

50. The system of claim 39, wherein the receptacle is a basket.

51. The system of claim 39, wherein the second set of openings are fenestrations.

52. A system for medical irrigation and tissue collection by introducing fluid into and withdrawing fluid from a body cavity, the system comprising:
a container having a container interior;
a cap demountably coupled to the container;
a portion for connection to a fluid line communicating with the body cavity;
a pump conduit;
a pump bulb demountably coupled to the pump conduit;
a basket disposed in the container interior, the basket having a first set of openings of a first size for permitting movement of fluid and particulate therethrough; and
a tube having a second set of openings of a second size for permitting movement of fluid and particulate therethrough, the tube further having a flanged portion demountably coupled to the basket and the tube being further coupled to the cap.

53. The system of claim 52, wherein the pump conduit extends from the cap.

54. The system of claim 52, wherein the first size is different from the second size.

55. The system of claim 52, wherein the second set of openings are radially disposed.

56. The system of claim 52, wherein the second set of openings arc fenestrations.

57. The system of claim 52, wherein the second set of openings are disposed along a substantial portion of the tube between free ends thereof.

58. The system of claim 52, wherein the flanged portion comprises a skirt, the flanged portion being demountably coupled to the basket at die skirt.

* * * * *

UNITED STATES PATENT AND TRADEMARK OFFICE
CERTIFICATE OF CORRECTION

PATENT NO. : 7,172,579 B2  
APPLICATION NO. : 10/841074  
DATED : February 6, 2007  
INVENTOR(S) : Barzell et al.

It is certified that error appears in the above-identified patent and that said Letters Patent is hereby corrected as shown below:

In claim 3, Col. 13, line 24, delete "area".

In claim 13, Col. 14, line 30, replace "arid" with --and--.

In claim 19, Col. 15, line 6, replace "articulate" with --particulate--, and in Col. 15, line 10, replace "container" with --container;--.

In claim 22, Col. 15, line 45, replace "portions wit" with --portions with--, and in Col. 15, line 48, replace "the pressure" with --pressure--.

In claim 27, Col. 16, line 18, replace "with upper" with --with the upper--.

In claim 36, Col. 17, line 16, replace "the lower portion" with --a lower portion--.

In claim 58, Col. 18, line 50, replace "die skirt" with --the skirt--.

Signed and Sealed this

Twenty-first Day of August, 2007

JON W. DUDAS  
*Director of the United States Patent and Trademark Office*